United States Patent [19]

Golub

[11] Patent Number: 5,120,224

[45] Date of Patent: Jun. 9, 1992

[54] LAMINATE WITH INTERNALIZED MATRIX OF FABRIC

[76] Inventor: Jeff E. Golub, 128 E. 71st St., New York, N.Y. 10021

[21] Appl. No.: 309,294

[22] Filed: Feb. 13, 1989

[51] Int. Cl.[5] .............................................. A61C 5/00
[52] U.S. Cl. .................................. 433/215; 433/202.1; 433/223
[58] Field of Search ..................... 433/215, 202.1, 223, 433/217.1, 219, 222.1

[56] References Cited

U.S. PATENT DOCUMENTS

| | | | |
|---|---|---|---|
| 2,755,552 | 7/1956 | Brandau | 433/215 |
| 4,433,960 | 2/1984 | Garito et al. | 433/215 |
| 4,504,229 | 3/1985 | Garito et al. | 433/215 |
| 4,728,291 | 3/1988 | Golub | 433/215 |
| 4,799,888 | 1/1989 | Golub | 433/215 |
| 4,894,012 | 1/1990 | Goldberg et al. | 433/215 |

*Primary Examiner*—Gene Mancene
*Assistant Examiner*—Michael Lynch
*Attorney, Agent, or Firm*—James P. Malone

[57] ABSTRACT

The process of fabricating a laminate, or series of attached laminates, with internalized matrix of fabric. The uses of such a process are to mask discolored, chipped, jumbled and spaced teeth with an ultra-thin, fabric based laminate which would require virtually no tooth reduction. Additional uses of fabric-encased laminates: missing teeth can be replaced with a chain of fabric laminates and pontics, loose teeth can be splinted with a fabric chain and missing teeth can be provisionally replaced with a pontic laminate attached to fabric, wherein the laminate is constructed of porcelain or composite and the internalized grid is made of fabric, such as polyester.

2 Claims, 7 Drawing Sheets

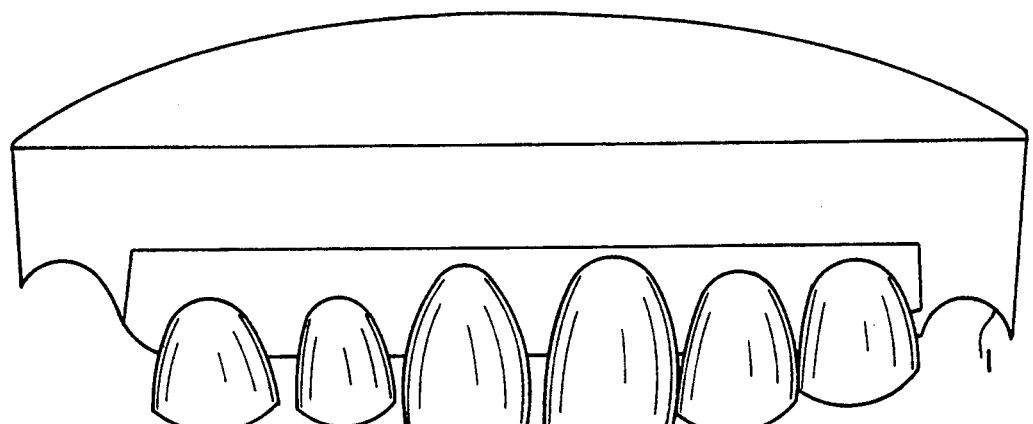
FIG. IA
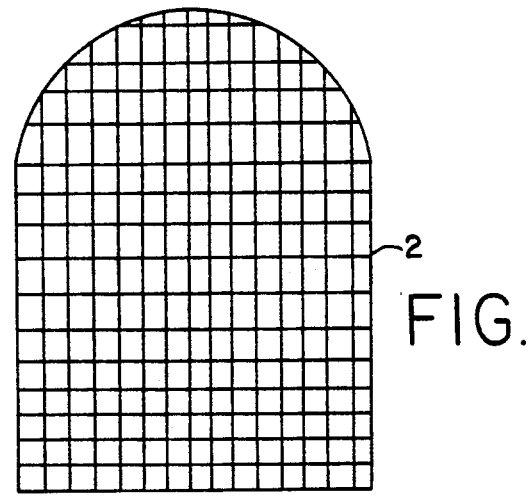
FIG. IB
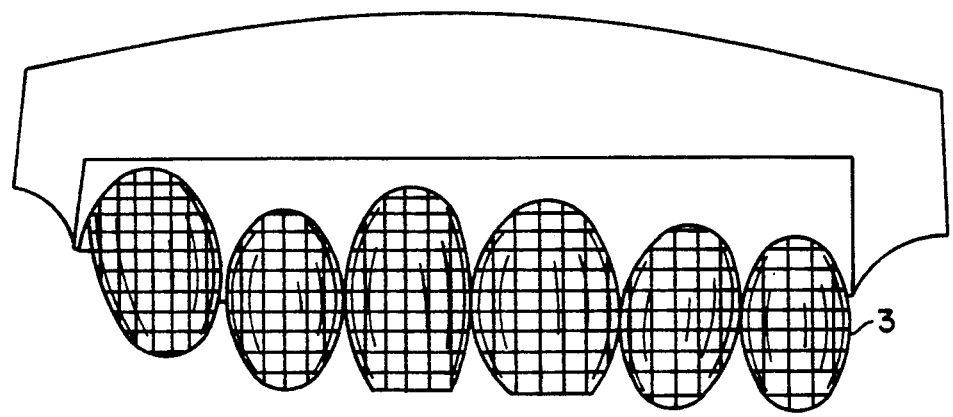
FIG. IC

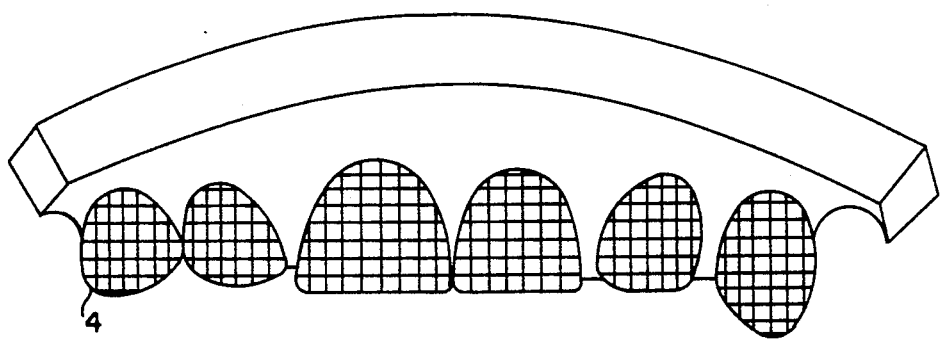
FIG. ID
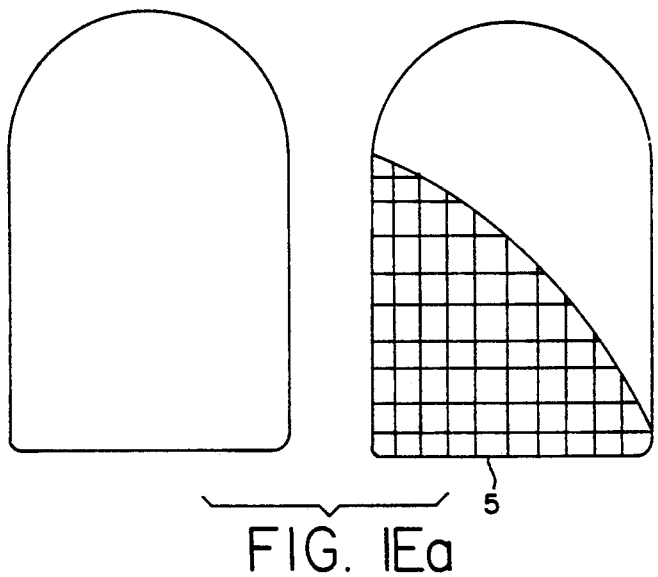
FIG. IEa
FIG. IEb
FIG. IEc
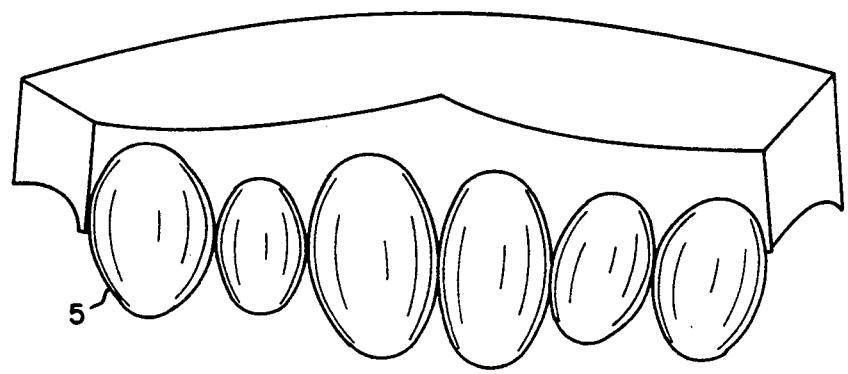
FIG. IF

LAMINATE WITH INTERNALIZED MATRIX OF FABRIC

This application is an improvement of my U.S. Pat. No. 4,728,291.

The abstract and the conclusions mentioned in U.S. Pat. No. 4,728,291 limits the fabric to silk or nylon. The author has been using polyester and other synthetic textiles which have superior tensile strength and shear strength to silk and yet maintain equivalent biocompatibility. U.S. Pat. No. 4,728,291 may be extended to include ALL FABRICS, including synthetic high-tensile strength textiles, orlons, dacrons, polyesters, and fabrics composed of new high performance fibers such as Kevlar, Sprectra 1000, glass, Vector and Alumina. The author has experimented with every manner of fabric and has concluded that the best materials presently available for the cloth wrap dental process are the synthetic high tensile strength fibers.

The author wishes additionally to apply for a patent to cover a laminate with internalized fabric and a chain of laminates with fabric inside.

BACKGROUND

The etched porcelain laminate (a.k.a. porcelain veneer) and composite laminate have been demonstrated clinically for six years, but both present major limitations. These materials are excellent for masking unsightly teeth and are readily bonded to tooth structure with a variety of dental bonding agents. Their limitations, however, are based upon construction of these items at a minimum thickness of 0.4 to 0.5 mm. Thinner laminates do not have adequate shear and tensile strength and shatter easily. Because of this, natural teeth need to be reduced considerably in order to compensate for the thickness of the laminate. Non-reduction of tooth enamel in advance of bonding the laminate can result in tissue inflammation because of the increased bulk at the gingival margin and also can result in over-built, overcontoured, esthetically unpleasing laminates. A need exists, therefore, to fabricate ultra-thin laminates which will require no (or at least minimal) tooth reduction.

A need additionally exists to replace missing teeth with a minimum of tooth reduction of the adjacent abutment teeth. For many years a variety of precious and non-precious alloys have been used as internal structural components in conventional full-coverage porcelain bridgework, but both of these methods require extensive tooth reduction and metallic frameworks. The Manhattan Bridge (Golub) has been demonstrated in the Cloth Wrap Dental Process, U.S. Pat. No. 4,728,291, to include the application of fabric to the abutment teeth, bonding the fabric to the teeth, and sculpting the missing tooth in free-handed composite. This system has worked well, but because it is a free-handed system, it is difficult for many clinicians to finish and polish. The framework of the silk-resin Manhattan Bridge is ultimately surfaced in composite resin and, therefore, the technique must be considered provisional in light of the five and ten year wear tests of direct composite techniques.

THE INVENTION

The author proposes an internalized grid-like skeleton of fibers, either woven or non-woven, bundled or individual. When incorporated into a laminate, a fabric grid can allow for extreme thinness of a laminate while continuing to maintain tensile strength, and allow for excellent esthetic results with virtually no tooth reduction. Should a section of the laminate become debonded due to an external force or an inadequate cohesive technique, the internalized fabric would remain adherant to the chipped piece and prevent it from becoming detached from the main body of the laminate. The laminate-fabric complex (Fabri-Lam) is superior to the Manhattan Bridge because the porcelain or composite is baked or cooked outside the mouth and is, therefore, less porous and more resistant to staining and chipping than the directly applied bonding material.

The author proposes that Fabric-wrapped laminates attached in a chain, with pontics sandwiched over the fabric could be used as well to replace missing teeth and would provide a more durable, predictable and tissue compatible result. The Fabri-Lam Bridge System utilizes an internal structural component of a high tensile strength fiber framework, around which the abutment laminates and pontics are fabricated. With this system, no tooth reduction is necessary to replace missing teeth.

Periodontal splinting is accomplished by fabricating a chain of laminates attached to fabric. Instead of reducing considerable tooth structure and placing full-coverage attached crowns to splint loose teeth together, a chain of Fabri-Lams, per this invention, can be constructed utilizing the labial and proximal surfaces of each tooth to be splinted. Minimal or no tooth reduction would be necessary.

Temporary or provisional bridges. At the present time the Manhattan Bridge can satisfy this need with minimum tooth reduction, but requires considerable skill of the operator to build a free-handed pontic. A Fabri-Lam System would provide pre-made pontics attached to wings of fabric which could be easily bonded to abutment teeth.

OBJECTS OF THE INVENTION

A principal object of the invention is to provide a new and improved process for manufacture of porcelain and composite laminates to include an internal structural component of fabric fiber arrangements.

Another object of the invention is to provide a chain of fabric laminates and pontics in porcelain or composite to create pre-made Manhattan Bridges which could replace missing teeth with minimal tooth structure.

Another object of the invention is to provide a temporary or provisional tooth replacement system which includes fabric strips embedded into a pre-made composite pontic. The fabric wings can then be easily bonded to the abutment teeth.

Another object of the invention is to provide a rigid grid, or a matrix, for both the technician and dentist to allow for proper shaping and coloring.

BRIEF DESCRIPTION OF THE DRAWINGS

FIG. 1a is a front view of an embodiment of the invention.

FIGS. 1b and 1c are detail front views of an embodiment of the invention.

FIG. 1d is a front view of an embodiment of the invention.

FIGS. 1e-A, 1e-B, 1e-C are detail views of an embodiment of the invention.

FIG. 1f is a front view of an embodiment of the invention.

BEST MODE OF THE INVENTION

I. Individual Fabric Embedded Laminates

1. The teeth to be laminated are cleansed. Virtually no tooth reduction or preparation is necessary because the fabric to be enclosed can represent only 32/100 of an inch. Elastomeric impression is taken of the teeth on which the laminates are proposed. The negative impression is poured in a stone or epoxy master model (FIG. 1A).

2. Individual high-tensile strength fabric matrices 2, 3, 4 of polyester are adapted to each tooth to be laminated on the model (FIG. 1b, 1c, 1d.). Some synthetic fabrics can be heat hardened to retain memory of the model. This stiffened piece can then act as a matrix or grid for the laminate overly. For porcelain, a refractory textile must be used. The fabric may be alumina or other high fusing fiber 3. The laminate material is layered over the fabric grid, totally embedding the textile in the composite or porcelain (FIG. 1e.). Average thickness with present technology can be merely 0.2 to 0.3 of a millimeter as opposed to non-fabric laminates of 0.5 to 0.7 mm. Further investigation will lead to even thinner laminates until a mere skin of composite or porcelain attached to fabric can be developed.

4. The laminate 5 (FIG. 1e, 1eA, 1eB, 1eC, 1f) is shaped and colored. Conventional ceramic or resin technique follows, including characterizing the laminate, placing in an oven, removing from the model, and etching the internal aspect.

5. The laminates are bonded in place with current dual-cured cementation methods (FIG. 1f.)

II. Fabric-Embedded Laminate Bridges

Figure 2A:
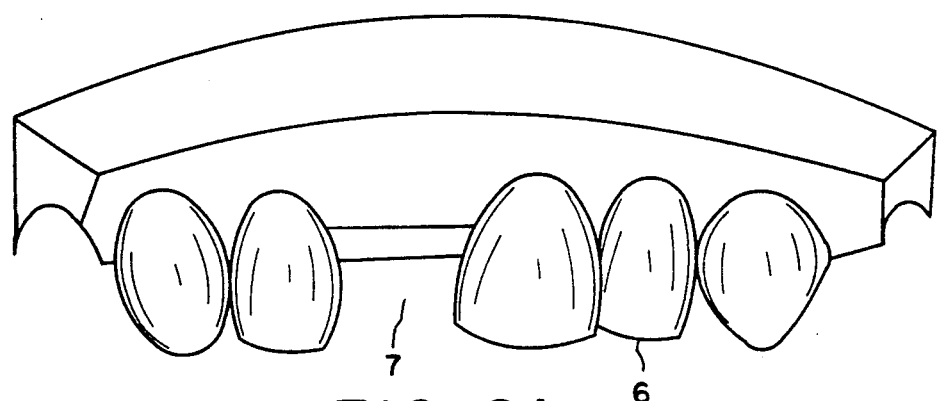
FIG. 2A is a front view of an embodiment of the invention designed to add a tooth.

1. The patient's teeth are cleansed, an elastomeric impression is taken, and a master model 6 is poured displaying the missing tooth 7 (teeth) and the adjacent abutment(s) (FIG. 2a.).

Figure 2B:
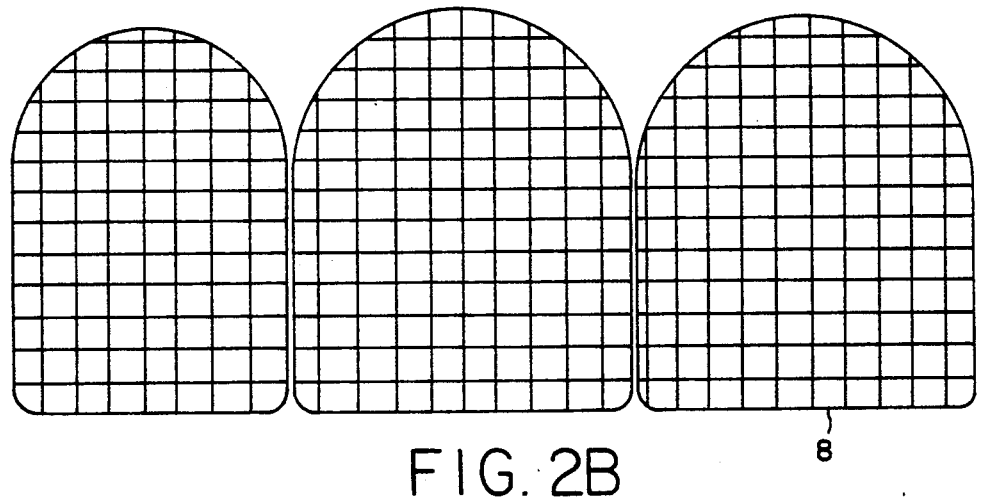
FIG. 2B is a front view of the embodiment of FIG. 2A.
Figure 2C:
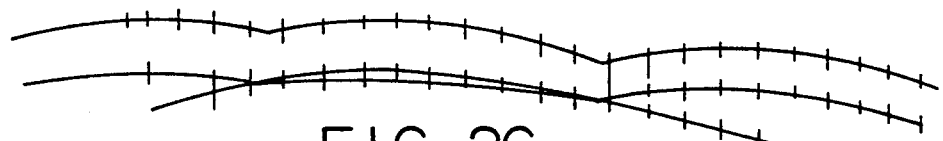
FIG. 2C is a top view of the embodiment of FIG. 2B.

2. A fabric chain 8 is cut and adapted to the model to fit over the pontic area (missing tooth) and the adjacent abutment teeth (FIG. 2b). Optionally a second piece of fabric 10 can be used if the operator wishes a 2-ply fabric to be internalized (FIG. 2c). Additional layers of fabric are possible based on strength and esthetic considerations.

Figure 2D:
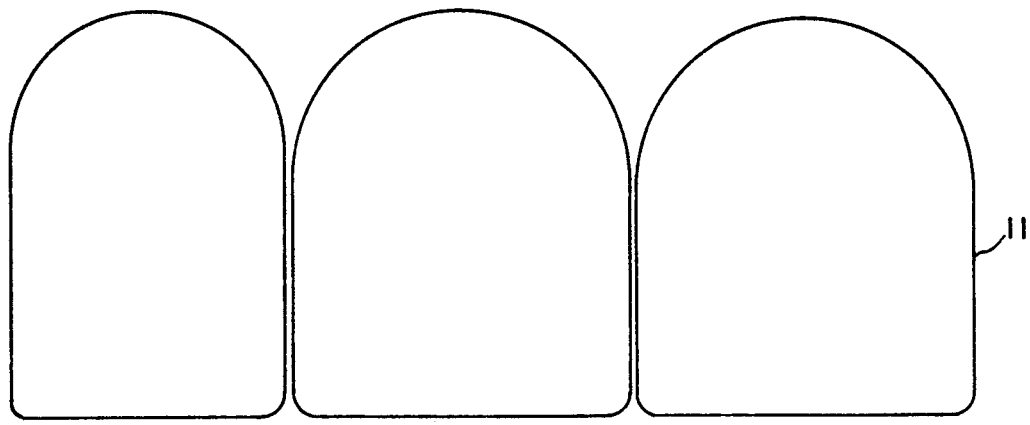
FIG. 2D is a front view of the embodiment of FIG. 2B.

3. The composite, or porcelain material, is then formed around the interstices of the cloth grid as a one piece item 11 (FIG. 2d). Additional composite or porcelain can be placed on the lingual aspect of the pontic, sandwiching the fabric to create a full-thickness tooth.

Figure 2E:
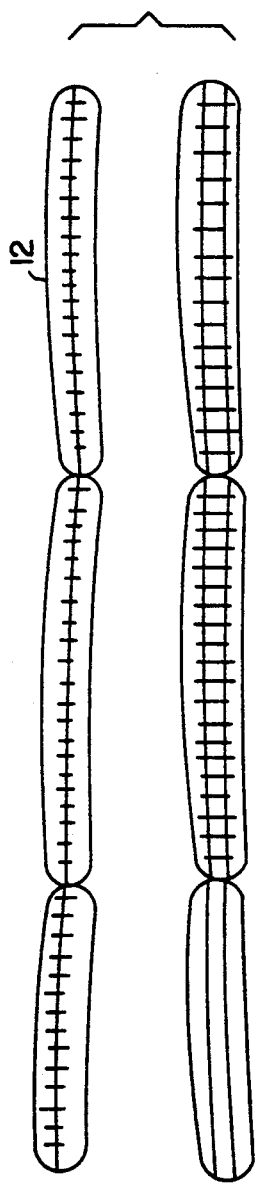
FIGS. 2E and 2F are detail views of the embodiment of FIG. 2D.

With option two, a secondary piece of fabric 12 can be used to create accessory adhesion on the lingual aspect of the abutment teeth and can minimize torqueing of the bridge (FIG. 2e).

Figure 2F:
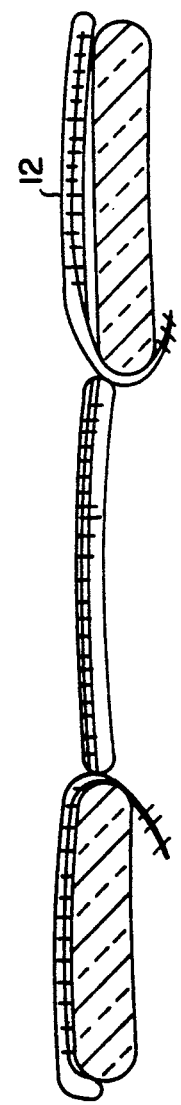

The bridge is bonded in place utilizing current dual-cured cementation methods. If the option of a second layer of fabric is used, the fabric wings can be bonded on the lingual aspect to provide additional support. (FIG. 2f).

III. Periodontal Splinting With a Chain of Fabric-Embedded Laminates

Figure 3A:
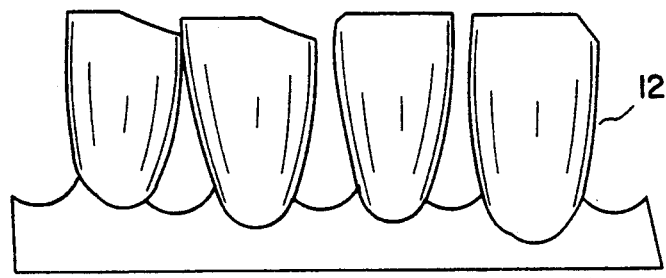
FIG. 3A is a front view of another embodiment of the invention.

1. The patient's teeth are cleansed, an elastomeric impression is taken, and a master model 12 is poured of the teeth to be splinted (FIG. 3a).

Figure 3B:
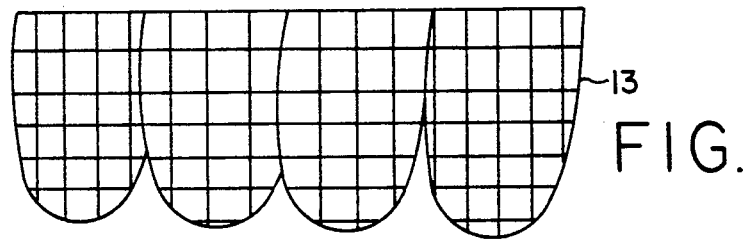
FIGS. 3B, 3C, 3D and 3E, are detail views of an embodiment of FIG. 3A.

2. A fabric chain 13 is cut and adapted to the model in the area to be splinted (FIG. 3b).

Figure 3C:
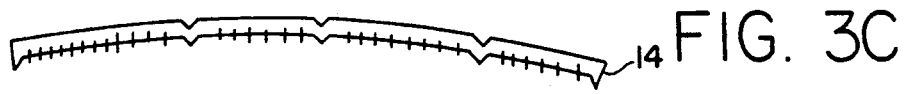
Figure 3D:
Figure 3E:
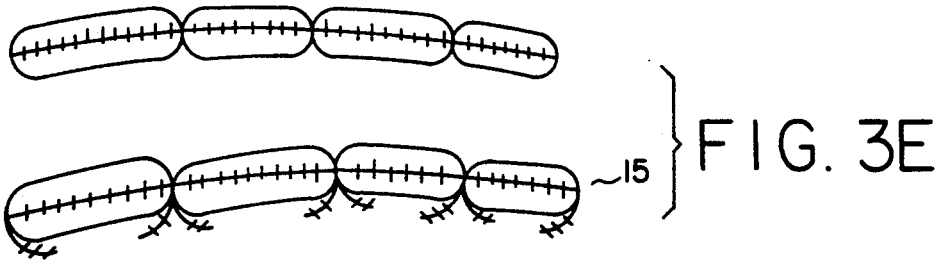

3. The restorative material 14, porcelain or composite, is attached to the fabric grid (FIG. 3c). Should a double thickness (2 ply) of fabric be used, accessory wings 15 of fabric can be placed interproximally to act as additional retention strips (FIG. 3d).

4. The laminate chain is bonded conventionally. Should the option of accessory lingual wings have been designed, they are bonded onto the lingual aspect as the laminates are bonded onto the facial aspect.

Figure 4A:
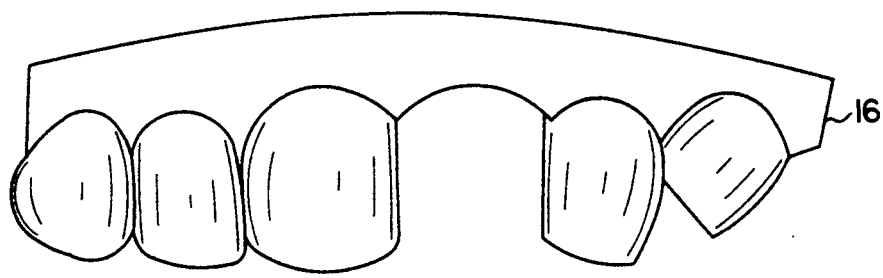
FIG. 4A is a front view of an embodiment replacing a tooth.

IV. Provisional or Temporary Bridge With Pre-Made Pontic and Embedded Fabric Wings 1. A case is selected demonstrating a missing tooth or a tooth that is scheduled for future extracting in a dental arch that provides two adjacent bondable teeth. A study model 16 is made of this defect or potential defect (FIG. 4a).

Figure 4B:
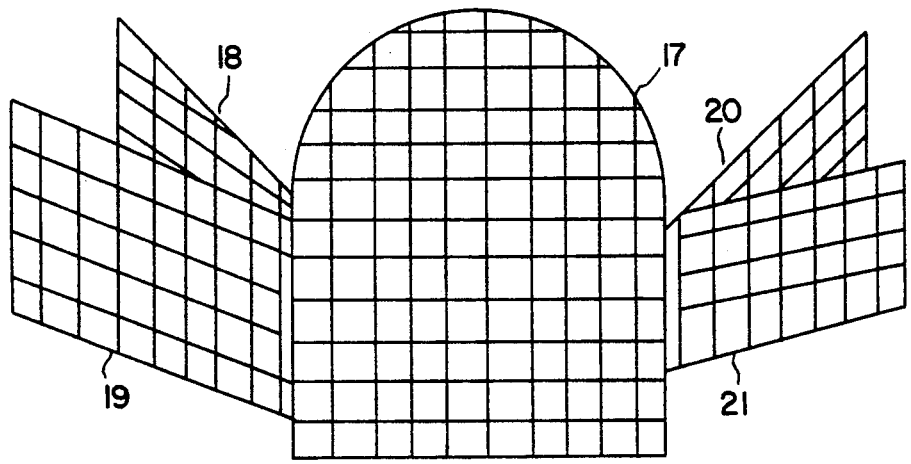
FIGS. 4B, 4C, 4D, 4E and 4F, are detail views of the embodiment of FIG. 4A.
Figure 4C:
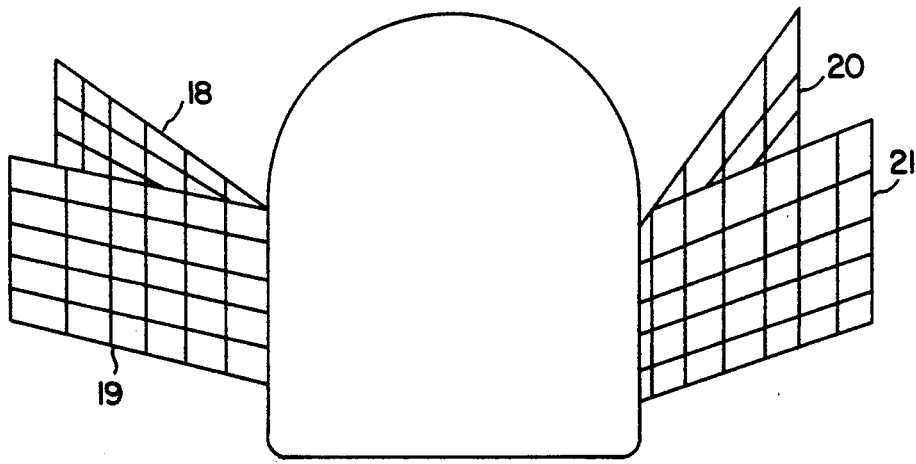
Figure 4D:
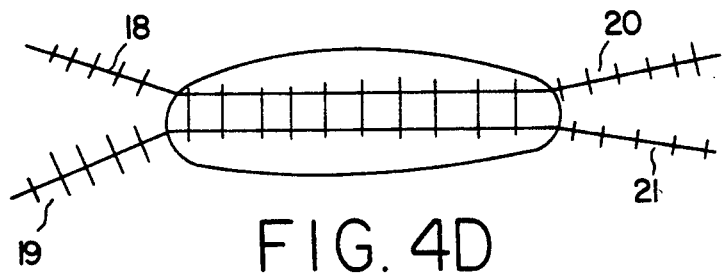

2. A double ply fabric grid 17 is constructed to approximate the lost tooth, or potentially lost tooth. Four wings 18, 19, 20, 21 of fabric are created to adhere on both the facial and lingual aspects of the abutment teeth (FIG. 4b).

3. The restorative material, porcelain or composite, is then layered and shaped over the pontic area, leaving the free wings of fabric available for facial and lingual bonding (4c, 4d).

Figure 4E:
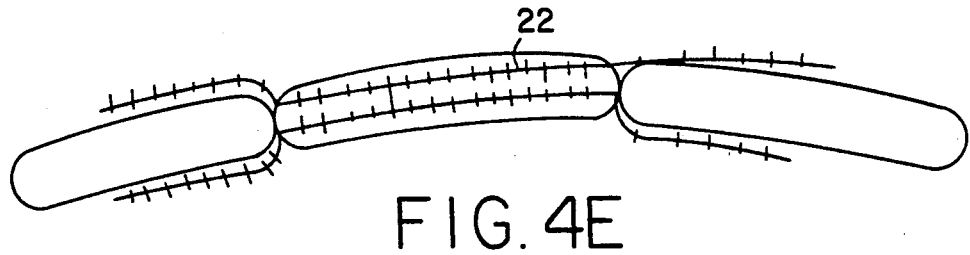
Figure 4F:
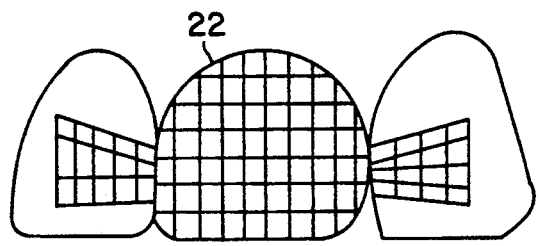

4. The pontic is bonded in place, utilizing the fabric wings 18-21. Additional composite 22 can be placed over the wings, especially facially, to create an esthetically pleasing result (FIGS. 4e, 4f).

5. Additionally, an inventory of pontic-fabric pieces in various sizes and colors, and for different specified teeth, can be constructed and delivered in kit form. The dentist would choose the pontic that best suits his purpose and would freely adapt the pontic as a chairside procedure. Each pontic would have the four wings of fabric which could be bonded into place. It is understood that such a stock item pontic would be constructed of a composite, or porcelain in this case, to allow for the customization of the pontic to the patient by addition and subtraction of composite, depending on whether the dentist had the equipment and/or training to allow him to customize the parts to the patient by addition or subtraction.

It is claimed:

1. The process of fabricating an ultra thin laminate of 0.2 to 0.3 millimeter with internalized matrix of fabric, to mask discolored, chipped, jumbled and spaced teeth with an ultra-thin fabric-based laminate which requires virtually no tooth reduction, comprising the steps of shaping a fabric matrix grid, layering a laminate material over the grid, shaping and coloring the laminate, curing the laminate in an oven, whereby missing teeth can be replaced with a chain of fabric laminates and pontics, loose teeth can be splinted with a fabric chain and missing teeth can be provisionally replaced with a pontic laminate attached to fabric, wherein the laminate is constructed of composite and the internalized grid is made of fabric.

2. Cosmetic dental means comprising an ultra thin cosmetic laminate of approximately 0.2 to 0.3 millimeters with internalized matrix of fabric, adapted to be applied to a tooth to mask discolored, chipped, jumbled and spaced teeth with an ultra-thin fabric-based laminate which requires virtually no tooth reduction, whereby missing teeth can be replaced with a chain of fabric laminates and pontics, loose teeth can be splinted with a fabric chain and missing teeth can be provisionally replaced with a pontic laminate attached to fabric, wherein the laminate is constructed of composite and the internalized grid is made of fabric.

* * * * *